(12) United States Patent
Winquist et al.

(10) Patent No.: US 6,682,531 B2
(45) Date of Patent: Jan. 27, 2004

(54) ORTHOPAEDIC BONE PLATE

(75) Inventors: Robert A. Winquist, Seattle, WA (US); Steve Benirschke, Seattle, WA (US); Paul Duwelius, Lake Oswego, OR (US); James Goulet, Ann Arbor, MI (US); Raymond Desjardins, Arnprior (CA); David Templeman, Plymouth, MN (US); John E. Meyers, Columbia City, IN (US); Stanley W. Patterson, Warsaw, IN (US); Gregory G. Price, Warsaw, IN (US)

(73) Assignee: Zimmer Technology, Inc., Chicago, IL (US)

( * ) Notice: Subject to any disclaimer, the term of this patent is extended or adjusted under 35 U.S.C. 154(b) by 312 days.

(21) Appl. No.: 09/938,071

(22) Filed: Aug. 23, 2001

(65) Prior Publication Data

US 2002/0065516 A1 May 30, 2002

Related U.S. Application Data

(63) Continuation of application No. 09/309,638, filed on May 11, 1999, now Pat. No. 6,355,042, which is a continuation of application No. 09/052,539, filed on Mar. 31, 1998, now Pat. No. 5,938,664.

(51) Int. Cl.$^7$ ................................................ A61B 17/58
(52) U.S. Cl. ............................ 606/69; 606/70; 128/898
(58) Field of Search .............................. 606/69, 70, 71; 128/898

(56) References Cited

U.S. PATENT DOCUMENTS 5,634,926 A * 6/1997 Jobe ............................ 606/69

* cited by examiner

Primary Examiner—Julian W. Woo
(74) Attorney, Agent, or Firm—Baker & Daniels

(57) ABSTRACT

An orthopaedic bone plate is coupled to a bone having an enlarged head at one end thereof which is attached to a shaft. The bone plate includes an elongate portion a flared portion and an intermediate portion. The elongate portion is attachable to the bone shaft using a plurality of bone screws. The elongate portion generally defines a longitudinal axis. The flared portion is attachable to the bone head using at least one bone screw. The intermediate portion interconnects the elongate portion and the flared portion. The intermediate portion is structured and arranged to allow the elongate portion and the flared portion to move relative to each other in a direction transverse to the longitudinal axis when the elongate portion and the flared portion are attached to the bone.

3 Claims, 2 Drawing Sheets

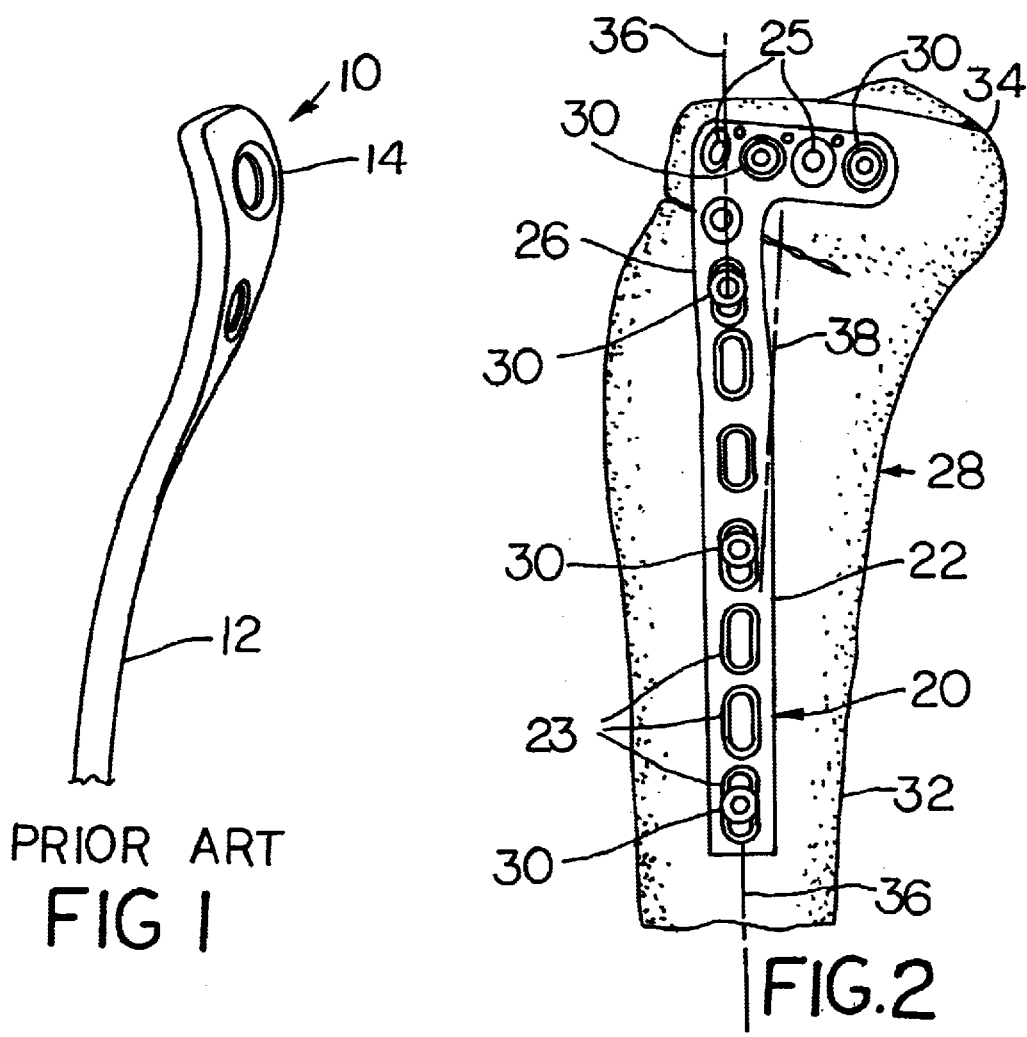
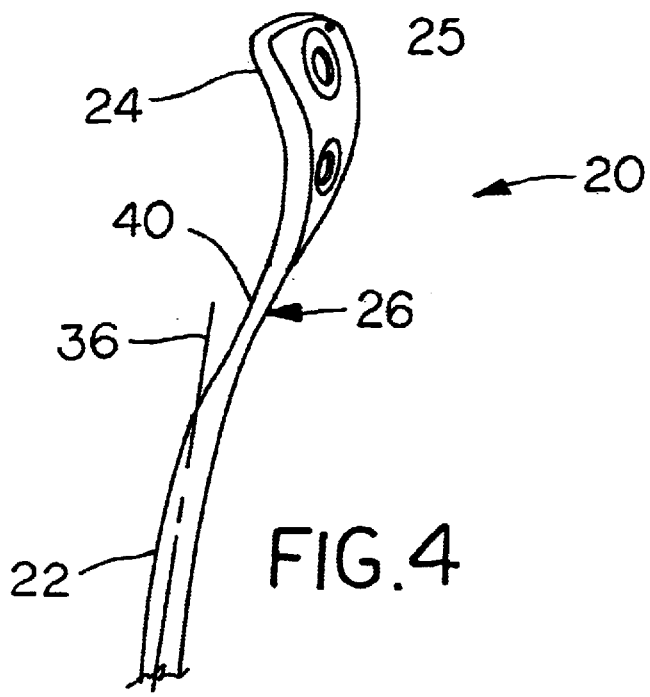

ORTHOPAEDIC BONE PLATE

This is a continuation of application Ser. No. 09/309,638, filed May 11, 1999, now U.S. Pat. No. 6,355,042 which is a continuation of application Ser. No. 09/052,539, filed on Mar. 31, 1998, which issued as U.S. Pat. No. 5,938,664 on Aug. 17, 1999.

BACKGROUND OF THE INVENTION

1. Field of the Invention

The present invention relates to orthopaedic bone plates, and, more particularly, to orthopaedic bone plates attached to an end and shaft of a bone.

2. Description of the Related Art

A bone plate is typically used to maintain different parts of a fractured or otherwise severed bone substantially stationary relative to each other during and/or after the healing process in which the bone mends together. Bones of the limbs include a shaft with a head at either end thereof. The head of a bone has a periphery which is either slightly or greatly enlarged relative to the periphery of the shaft to provide a larger load bearing surface at the end of the bone. Fractures of a bone in the region of the head may be particularly troublesome because of moving and/or soft tissues in the region of the bone joint.

It is known to provide a bone plate which attaches to both a head and the shaft of the bone to thereby maintain the head substantially stationary relative to the shaft. Such a bone plate includes an elongate portion which attaches to the shaft of the bone and a flared portion which attaches to the head of the bone using a plurality of bone screws. The elongate portion and the flared portion are both relatively thick in a direction transverse to the anatomical axis of the bone shaft such that the head and shaft of the bone do not move relative to each other after the bone plate is attached to the bone.

With a conventional bone plate as described above, the flared portion may be curved to accommodate the enlarged curvature of the head. It is quite common for the curvature of the flared portion to not exactly correspond to the curvature of the bone head. Rather, the bone plate has a shape corresponding to a shape of an average bone based upon statistical data. The relatively thick bone plate thus in essence provides a buttress roadmap for the surgeon to reconstruct the bone or place fragments of the bone against the bone plate during the reconstruction.

It is common practice with a thick bone plate as described above for an orthopaedic surgeon to place such a bone plate against the bone, observe the differences in curvature between the bone plate and bone, remove the bone plate and hammer or otherwise bend the bone plate to better fit the bone, and again place the bone plate against the bone. This process is repeated until a satisfactory fit is achieved between the bone plate and the bone.

What is needed in the art is a bone pate which more easily conforms to the shape of a bone without manually and permanently deflecting the bone plate with repeated fitting steps by trial and error.

SUMMARY OF THE INVENTION

The present invention provides an orthopaedic bone plate with a flared portion which can deflect toward and thereby conform to the shape of a bone when the elongate portion and flared portion are screwed to the bone. When attached to the bone, the bone plate also acts as a buttress surface with an improved anatomical approximation for smaller bone fragments.

The invention comprises, in one form thereof, an orthopaedic bone plate coupled to a bone having an enlarged head at one end thereof which is attached to a shaft. The bone plate includes an elongate portion, a flared portion and an intermediate portion. The elongate portion is attachable to the bone shaft using a plurality of bone screws. The elongate portion generally defines a longitudinal axis. The flared portion is attachable to the bone head using at least one bone screw. The intermediate portion interconnects the elongate portion and the flared portion. The intermediate portion is structured and arranged to allow the elongate portion and the flared portion to move relative to each other in a direction transverse to the longitudinal axis when the elongate portion and the flared portion are attached to the bone.

An advantage of the present invention is that the bone plate conforms to the shape of the bone by simply screwing the elongate portion and flared portion of the bone plate to the bone.

Another advantage is that the bone plate need not be manually bent or otherwise permanently deformed prior to being attached to the bone.

Yet another advantage is that an improved anatomical approximation of the bone plate is achieved through deflection of the bone plate, thereby resulting in superior bone reduction at the fracture.

A further advantage is that the improved anatomical approximation results in an increased contact interface between the bone plate and bone, resulting in moreloading on the bone and less loading on the bone plate with a reduced possibility of fatigue failure of the bone plate.

A still further advantage is that the superior reduction of the bone results in improved loading between the bone pieces at the fracture site, resulting in improved healing.

An additional advantage is that the improved anatomical approximation results in an improved alignment of the articular surface at the joint of the bone, thereby inhibiting premature wear of the bone.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 1 is a side, fragmentary view of a conventional bone plate;

FIG. 2 is a perspective, fragmentary view of an embodiment of a bone plate of the present invention attached to a bone;

FIG. 4 is a side, fragmentary view of the bone plate of FIGS. 2 and 3; and

Corresponding reference characters indicate corresponding parts throughout the several views. The exemplification set out herein illustrates one preferred embodiment of the invention, in one form, and such exemplification, is not do be construed as limiting the scope of the invention in any manner.

DETAILED DESCRIPTION OF THE INVENTION

Figure 3:
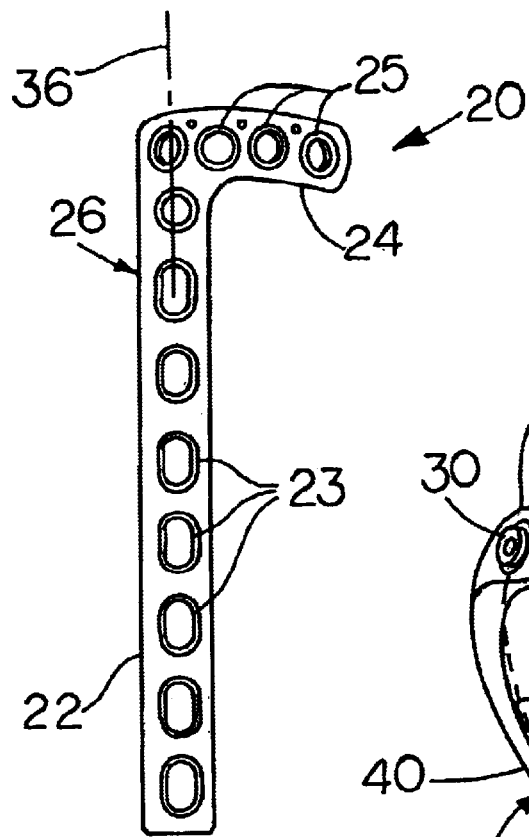
FIG. 3 is a front view of the bone plate of FIG. 2.

Referring now to the drawings, and particularly to FIG. 1, there is shown a side, fragmentary view of a conventional bone plate 10 including an elongate portion 12 and a flared portion 14. It may be seen that the thickness of elongate portion 12 and flared portion 14 are both substantially the same in FIG. 1. Such a conventional bone plate has a thickness which does not allow the bone plate to deflect without hammering or using other tools. Of course, the bone plate cannot be deflected while on the patient while using such tools. The bone plate must therefore be fitted to the bone and thereafter removed to place a permanent bend therein.

Although bone plate 10 shown in FIG. 1 has a relative constant thickness between the elongate portion and the flared portion, the thickness may also slightly taper from the elongate portion to the flared portion. In either event, the thickness of known bone plates is such that the bone plate will not deflect after being attached to the bone, but rather must be bent or otherwise permanently deflected prior to being attached to the bone.

Figure 5:
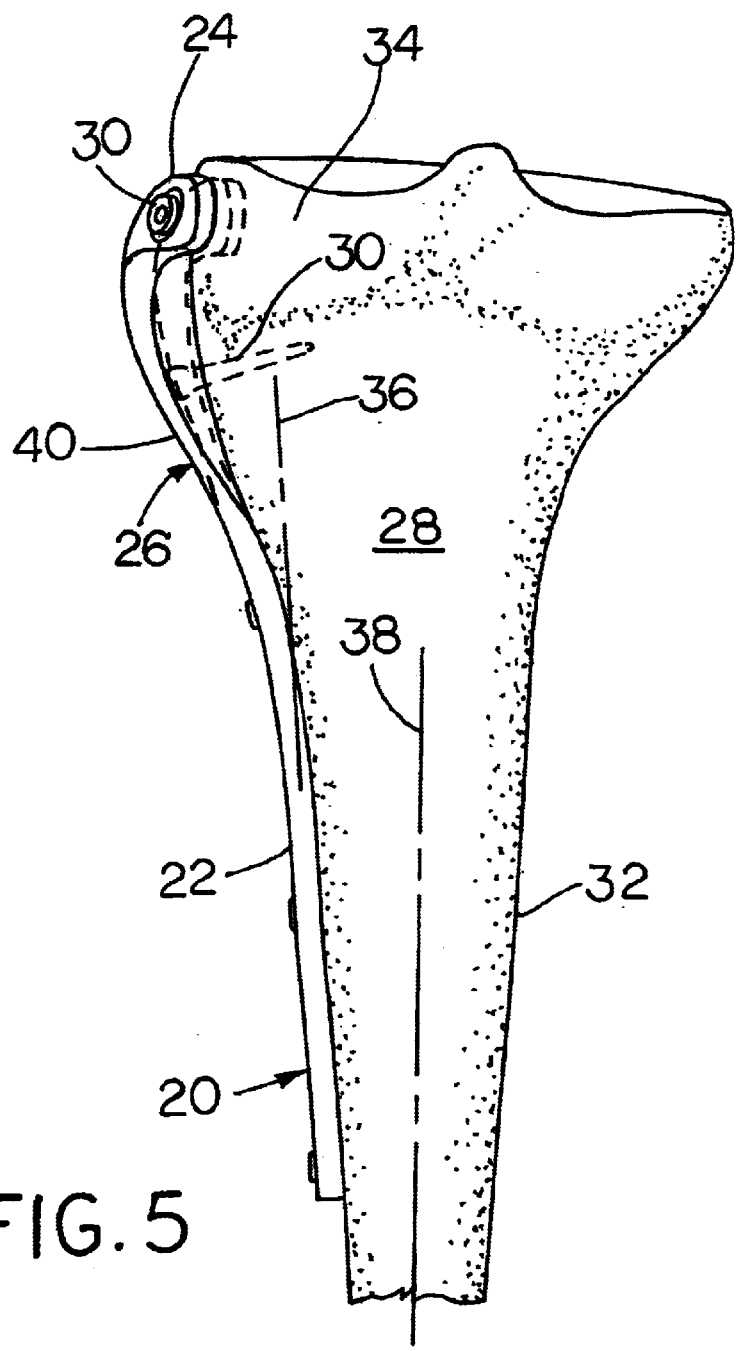
FIG. 5 is a side view of the bone plate of FIGS. 2–4 illustrating deflection or the flared portion and intermediate portion toward the bone.

Referring now to FIGS. 2–5, there is shown an embodiment of a bone plate 20 of the present invention. Bone plate 20 includes an elongate portion 22, a flared portion 24 and an intermediate portion 26. As shown in FIG. 2, bone plate 20 may be attached to a bone, such as the proximal end of a tibia 28, using a plurality of bone screws 30. Tibia 28 includes a shaft 32 and an enlarged head 34 at one end thereof. Shaft 32 defines an anatomical axis of tibia 28.

Elongate portion 22 includes screw holes 23 allowing attachment to bone shaft 32 using a plurality of bone screws 30. In the embodiment shown, three bone screws 30 are used to attach elongate portion 22 to shaft 32; however, a different number of bone screws may also be utilized. Elongate portion 22 generally defines a longitudinal axis 36 which is disposed generally parallel to anatomical axis 38 of tibia 28. Of course, it will be appreciated that longitudinal axis 36 and anatomical axis 38 are not likely perfectly parallel with each other.

Flared portion 24 includes screw hole 25 allowing attachment to head 34 of tibia 28 using at least one bone screw 30. In the embodiment shown, two bone screws 30 are used to attach flared portion 24 with head 34; however, a different number of bone screws 30 may be used.

Intermediate portion 26 interconnects elongate portion 22 with flared portion 24 of bone plate 20. Intermediate portion 26 is configured to allow elongate portion 22 and flared portion 24 to move relative to each other in a direction transverse to each of longitudinal axis 36 and anatomical axis 38 when elongate portion 22 and flared portion 24 are attached to tibia 28. More particularly, intermediate portion 26 is formed with a thin region 40 which allows intermediate portion 26 to deflect in a direction generally towards longitudinal axis 36 when elongate portion 22 and flared portion 24 are attached to tibia 28. That is, bone plate 20 is attached to tibia 28 using a plurality of bone screws 30, as indicated above. Each of bone screws 30 has a shear strength within the bone after being fully seated in the bone and against bone plate 20. Thin region 40 is configured such that bone plate 22 bends or deflects when bone screws 30 are seated against bone plate 20 and into tibia 28. The relative thinness of bone plate 20 in thin region 40 thus depends in part upon the shear strength between bone screws 30 and tibia 28.

It is of course also possible to configure the thinness of bone plate 20 in thin region 40 such that intermediate portion 26 moves toward head 34 when a predetermined loading is applied thereto which is less than and not related to the shear strength of bone screws 30 within tibia 28. Configuring bone plate 20 to deflect at such a lower loading value ensures that intermediate portion 26 and flared portion 24 move toward head 34, rather than head 34 moving toward flared portion 24 (which may not be desirable for purposes of bone alignment).

To further ensure that bone plate 20 propenly conforms to tibia 28, each of elongate portion 22, flared portion 24 and intermediate portion 26 are provided with a curvature on the surface abutting tibia 28 which defines a compound curvature corresponding to the typical shape of tibia 28. The compound curvature is derived from statistical data for the shape of a particular bone to which bone plate 20 is applied. That is, the compound curvature of bone plate 20 shown in FIGS. 2–5 for placement against a tibia 28 is likely different from the compound curvature of a bone plate attached to a different type of bone.

Aside from being configured to deflect in intermediate portion 26 toward longitudinal axis 36, bone plate 20 may also be configured such that flared portion 24 independently deflects toward head 34 of tibia 28. Thus, although flared portion 24 is slightly thicker than intermediate portion 26, flared portion 24 may also independently deflect toward longitudinal axis 36 and anatomical axis 38.

During orthopaedic surgery, bone plate 20 is placed against tibia 28 such that elongate portion 22 lies against bone shaft 32 and flared portion 24 lies against head 34. Elongate portion 22 is attached to bone shaft 32 using a plurality of bone screws 30. Flared portion 24 is attached to bone head 34 using at least one bone screw 30. When elongate portion 22 and flared portion 24 are each attached to tibia 28, intermediate portion 26 and flared portion 24 deflect toward anatomical axis 38 of tibia 28, thereby allowing bone plate 20 to conform to the peripheral shape of tibia 28.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of attaching an orthopedic bone plate to a bone comprising the steps of:

providing an orthopedic bone plate having an elongate portion generally defining a longitudinal axis, and a thinned portion having a decreased relative thickness adjacent to and integral with said elongate portion;

positioning the bone plate against the bone;

attaching said elongate portion to the bone using a first bone screw;

attaching said thinned portion to the bone using a second bone screw; and deflecting said thinned portion, dependent upon at least one of said attaching steps, such that said thinned portion moves in a direction transverse to the longitudinal axis.

2. The method of claim 1, wherein said deflecting step occurs as a result of said second attaching step.

3. The method of claim 1, wherein said deflecting step occurs as a result of said first attaching step.

* * * * *